United States Patent [19]

Plum et al.

[11] 4,112,084
[45] Sep. 5, 1978

[54] BACTERICIDAL AND FUNGICIDAL TIN COMPOUNDS

[75] Inventors: Hans Plum, Hamm-Heessen; Ulrich Schroeer, Kamen-Methler, both of Fed. Rep. of Germany

[73] Assignee: Schering Aktiengesellschaft, Berlin and Bergkamen, Fed. Rep. of Germany

[21] Appl. No.: 853,854

[22] Filed: Nov. 22, 1977

[30] Foreign Application Priority Data

Dec. 29, 1976 [DE] Fed. Rep. of Germany ....... 2659288

[51] Int. Cl.² ...................... A01N 9/20; C07C 117/00
[52] U.S. Cl. .................................... 424/226; 260/349
[58] Field of Search ......................... 424/226; 260/349

[56] References Cited

U.S. PATENT DOCUMENTS

| 3,112,331 | 11/1963 | Washburn et al. | 260/349 |
| 3,187,020 | 6/1965 | Minisci et al. | 260/349 |
| 3,232,958 | 2/1966 | Washburn | 260/349 |

*Primary Examiner*—Allen J. Robinson
*Attorney, Agent, or Firm*—Curtis, Morris & Safford

[57] ABSTRACT

Tri-isobutyl-tin azide, (i-Bu)₃SnN₃ is disclosed, as are certain bis-(azido-di-alkyl-tin)-oxides of the formula

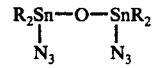

and a method for making them, as well as bactericidal and fungicidal agents comprising these biocidal tin compounds.

6 Claims, No Drawings

BACTERICIDAL AND FUNGICIDAL TIN COMPOUNDS

The present invention pertains to certain triorganotin azides, to certain bis-(azido-diorgano-tin)-oxides, to a method for making such oxides, and to bactericidal and fungicidal agents containing compounds of these types and having bactericidal and fungicidal activity. Such agents are suitable for use as disinfecting agents, wood protective agents, for imparting bactericidal and fungicidal properties to plastics, building materials, or textiles, or for use as biocidal paints.

The high activity of triorganotin compounds against microorganisms such as damaging fungi and bacteria is known. The tributyltin compounds, in particular tributyltin fluoride and bis-(tributyltin) oxide, have proved to be particularly effective. The high activity of the tributylin compounds against bacteria, however, is limited to gram-positive bacteria: against gram-negative bacteria they are considerably less effective. Tripropyltin compounds, which, however, because of their penetrating repulsive odor have found no practical employment, behave exactly contrarily: they are strongly inhibitory of gram-negative bacteria and less so of gram-positive bacteria.

These observations, in connection with a series of further tests, have heretofore led only to the conclusion that the biocidal behavior of triorganotin compounds was determined by the chain-length of the hydrocarbon group bound to tin, whereas the nature of the substituents not bound by carbon to tin was only of subordinate significance for the biocidal effect. [On this point, see A. Bokranz and H. Plum Fortschritte der chemischen Forschung, Vol. 16, Part ¾, pages 376– 379, Springer Verlag, Berlin, Heidelberg, New York (1971).]

Diorganotin compounds having an effect worth mentioning against microorganisms are only individually described, for example in German Auslegeschrift No. 25 26 711.

The present invention relates to biocidal and fungicidal agents which are characterized by a content of at least one compound of the formula $$Bu_3SnN_3 \tag{I}$$

in which Bu is n-butyl or isobutyl, or of the formula

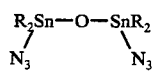

$$\tag{II}$$

wherein R is alkyl having 3-5 carbon atoms. A method for making the compounds of formula II by reacting dialkyltin dichloride with equimolar amounts of an alkali azide and an alkali hydroxide in polar solvents with stirring at room temperature is also discussed.

Preferred new active agents are:

Tri-isobutyl-tin azide, bis-(azido-di-n-propyl-tin)-oxide, bis-(azido-di-n-butyl-tin)-oxide, bis-(azido-di-i-butyl-tin)-oxide, and bis-(azido-di-n-pentyl-tin)-oxide.

Compounds having formula II are stannoxanes. It is known from the literature that stannoxanes are in equilibrium with the corresponding organotin hydroxides. The position of the equilibrium depends, among other things, on the organic residue bound to tin and on the solvent [cf. W. P. Neumann, Die org. Chemie des Zinns, Ferd. Enke Verlag, Stuttgart (1967), Chapter 17.1, and A. K. Sawyer, "Organotin Compounds", M. Dekker, Ind., New York (1971) Chapter 4. 1A]. Thus, a simultaneous presence of $R_2Sn(OH)N_3$ in compounds having formula II cannot be excluded, particularly if their preparation takes place in an aqueous medium.

The compounds to be used as biocidal agents according to the present invention are insensitive to shock and impact. On dry heating, they slowly give off nitrogen and decompose to a black-brown residue without tendency toward explosion. Because of their difficult solubility in water, the organotin azides show only a slight tendency to hydrolyze.

The preparation of the organo-tin azides takes place by the reaction of triorganotin chlorides for diorganotin dichlorides with azides, for example $NaN_3$, according to the following equations (1) and (2):

$$R_3SnCl + NaN_3 \rightarrow R_3SnN_3 + NaCl \tag{1}$$

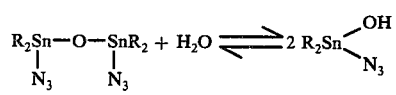

Reaction (2), in particular, involves the reaction of a dialkyl-tin dichloride with substantially equimolar amounts of an alkali metal azide, such as sodium azide or potassium azide, and of an alkali metal hydroxide, such as sodium hydroxide or potassium hydroxide. The reaction proceeds at room temperature by stirring the reagents in a polar solvent such as water; acetone (and in particular in mixtures of water and acetone); ethers, particularly diethyl ether; and alcohols, particularly methanol and ethanol.

Surprisingly, the organotin azides which are to be employed according to the invention and which can be prepared in a simple manner in part show a greater activity than the heretofore known tributyltin compounds or diorganotin compounds. Further, their activity spectrum extends also to the gram-negative bacteria.

The bactericidal and fungicidal efficacy of the organotin azides are evident from following Tables 1 and 2. Bis-(tributyltin) oxide (TBTO) was chosen as a substance for purposes of comparison.

For carrying out the biocidal test, nutrient agar was poured into petri dishes having a diameter of 10 cm. After solidification of the agar, the paper filters to be tested were placed thereon and sprayed with slurries of test bacteria or test fungi.

Normalization of the concentration of the test bacteria or test fungi was photometrically determined by means of a 1 cm-thick cuvette.

The extinction of the slurry was measured with a Zeiss PMQ 2 spectrophotometer. At 420 microns, the following extinction values were measured against water: (Selection)

*Aspergillus niger* 0.5
*Penicillium funiculosum* 0.8
*Bacillus mesentericus* 1.3
Bacillicus subtilis 1.3

Subsequently the fungi were cultured for 3 weeks at 30° C. and the bacteria for 2 to 4 days at 37° C.

The biocidal effect was evaluated according to the strength of the growth as well as the size of the inhibition zone around the samples Preparation of the samples:

Round filters of 5.5 cm diameter were saturated with ethanolic solutions of various concentrations and subsequently dried in air at room temperature. Concentration of the azide on the filter: 2.0/1.0/0.5/0.2%

Test bacteria:
Bacillus subtilis ATCC 6633
Bacillus mesentericus ATCC 945
Escherichia coli ATCC 10 536

Test fungi:
Aspergillus niger CBS 420.64
Pullularia pullulans BAH P 268
Penicillum funiculosum CBS 170.60

Test media:
Biomalt-agar 8° [measured in a Balling saccharometer at 20° C.](for fungi)
Plate-count-agar (for bacteria)

Results:

Table I

| | Bacteria | | |
|---|---|---|---|
| | Zone of inhibition around the samples in mm. | | |
| Content of Active Agent | Bac. mes | Bac. subt. | E. coli |
| None | 0 | 0 | 0 |
| 2.0% TBTO | 12–15 | 12–15 | 0–1 |
| 1.0% " | 10 | 12–15 | 0 |
| 0.5% " | 9–10 | 12–15 | 0 |
| 0.2% " | 8 | 12 | 0 |
| 2.0% nBu$_3$Sn-azide | 12–15 | 10 | 1 |
| 1.0% " | 12–15 | 10 | 0–1 |
| 0.5% " | 12–15 | 10 | 0 |
| 0.2% " | 10 | 10 | 0 |
| 2.0% i-Bu$_3$Sn-azide | 15 | 15 | 0 |
| 1.0% " | 15 | 12–15 | 0 |
| 0.5% " | 15 | 10–12 | 0 |
| 0.2% " | 12–15 | 10 | 0 |

Table I

| | Bacteria (continued) | | |
|---|---|---|---|
| | Zone of Inhibition around the samples in mm. | | |
| Content of Active Agent | Bac. subt. | Bac. mes. | E. coli |
| 2.0% Azido-(di-n-butyl-tin)-oxide | 3 | 4–5 | 2–3 |
| 1.0% " | 3 | 4 | 1–2 |
| 0.5% " | 2–3 | 3–4 | 1 |
| 0.2% " | 2–3 | 2–3 | 1 |
| 2.0% Azido-(di-i-butyl-tin)-oxide | 10 | 12–15 | 6–7 |
| 1.0% " | 9 | 10 | 5 |
| 0.5% " | 8 | 7–8 | 4 |
| 0.2% " | 7–9 | 8 | 3–4 |
| 2.0% Azido-(di-n-propyl-tin)-oxide | 10 | 12–15 | 7 |
| 1.0% " | 9 | 10 | 5–6 |
| 0.5% " | 8 | 8 | 4 |
| 0.2% " | 7 | 8 | 3–4 |
| 2.0% Azido-(di-n-pentyl-tin)-oxide | 9 | 13 | 6 |
| 1.0% " | 8 | 9 | 4–5 |

Table I-continued

| | Bacteria (continued) | | |
|---|---|---|---|
| | Zone of Inhibition around the samples in mm. | | |
| Content of Active Agent | Bac. subt. | Bac. mes. | E. coli |
| 0.5% " | 7 | 8 | 4 |
| 0.2% " | 6 | 7 | 3 |

Table 2

| | Fungi | | | | | |
|---|---|---|---|---|---|---|
| Content of Active Growth | Asp. nig. Growth on Sample | Zone of Inhibition (mm) | Pull.pull. Growth on Sample | Zone of Inhibition | Pen.fun. Growth on Sample | Zone of Inhibition (mm) |
| 0 | ++++ | 0 | ++++ | 0 | ++++ | 0 |
| 2.0% TBTO | − | 5 | − | 3 | − | 1 |
| 1.0% " | − | 4–5 | − | 2–3 | − | 0–1 |
| 0.5% " | − | 4 | − | 2 | +R | 0 |
| 0.2% " | − | 1 | − | 0–1 | ++ | 0 |
| 2.0% n-Bu$_3$Sn-azide | − | 9 | − | 10 | − | 1 |
| 1.0% " | − | 8–9 | − | 4 | − | 0–1 |
| 0.5% " | − | 3 | − | 1–2 | − | 0–1 |
| 0.2% " | − | 1 | − | 0 | +R | 0 |
| 2.0% i-Bu$_3$Sn-azide | − | 12–15 | − | 12–15 | − | 0 |
| 1.0% " | − | 10–12 | − | 12–15 | I | 0 |
| 0.5% " | − | 3–4 | − | 10–12 | I | 0 |
| 0.2% " | − | 1 | − | 3–4 | I | 0 |

Legend: −no growth; + light growth; ++ moderate growth; +++ strong growth; ++++ very strong growth
R = edge growth; I = Test fungus became infected with a foreign fungus.

The organotin azides to be used according to the invention can be employed alone, in admixture with each other, or in admixture with other active agents such as quaternary ammonium bases or phenolic compounds.

The organotin azides are suitably employed in the form of preparations such as solutions, dispersions, or with solid carriers or diluents, optionally in the presence of wetting agents, adhering agents, emulsifying agents, and dispersing agents. Suitable liquid carriers are, for example, methanol, ethanol, toluene, and xylene. As solid carriers, diatomaceous earth, siliceous clay, silica gel, kaolin, or talc are suitable, for example. Suitable surface-active substances are, above all, the non-ionic polethylene glycols.

Suitable formulations are given below, with the percentages by weight: Tri-isobutyl-tin azide in toluene as a 2% solution; tri-n-butyl-tin azide with 3 parts of emulsifier comprising alkyl-aryl-polyglycol ether as a 1% aqueous emulsion; bis-(azido-di-n-butyl-tin)-oxide on talc as a 2% strewable powder; bis-(azido-di-isobutyl-tin)-oxide as a 1% dilution with bleaching earth; and bis-(azido-di-n-pentyl-tin) oxide as a 5% solution in ethanol.

The agent can be applied in any desired fashion, for example by injection, immersion, spraying, dusting or painting.

The concentration of the active material in the biocidal agent can vary within relatively wide limits. It depends on the kind of the micoorganism to be combatted as well as on the substrate (wood, textiles, etc.). It is between about 0.1% and 3% by weight, based on the biocidal agent. In the preventive treatment of substrates, smaller concentrations would be chosen than when combatting microorganisms already present. Since the organotin azides according to the invention are only difficultly soluble in water, they can advantageously be used outdoors where they are exposed to weathering.

A better understanding of the present invention and of its many advantages will be had by referring to the following examples, given by way of illustration.

EXAMPLE 1

65.1 g of tri-isobutyl-tin chloride (0.2 mol) are dissolved in 100 ml of ether. This solution is run into another solution of 15.4 g of sodium azide (0.237 mol) in 80 ml of water and 40 ml of acetone. After stirring for ½ hour, the phases are separated. After driving off the ether, a tri-isobutyl-tin azide product remains whose Cl-value is 0-2.3%. The yield is ca. 80%. C found = 44.21% (theory = 43.41%); H = 8.74 found (8.20 theory); $n_D^{20}$: 1,5009.

EXAMPLE 2

In a fashion analogous to that above, the following materials were reacted: 30.30 g (0.1 mol) of di-isobutyl-tin-dichloride in 100 ml of ether and 15.4 g of sodium azide (0.237 mol) dissolved in water/acetone. After 4 hours' stirring, 4 g (0.1 mol) of NaOH were added. The solid white product precipitates in a yield of 26 g, which is 90% based on the formula i-Bu$_2$(N$_3$)SnOSn(N$_3$)i-Bu$_2$. It melts at 172°-174° C. Elemental analysis gave the following values [theoretical values are based on i-Bu$_2$(N$_3$)SnOSn(N$_3$)i-Bu$_2$]: C: 33.69 (32.92 ) %; H:6.65 (6.56) %; N: 12.97 (14.39)%; Cl: 0.87 (0)%; Sn:41.70 (40.65) %.

EXAMPLE 3

Example 2 was repeated using di-n-butyl-tin dichloride to prepare bis-(azido-di-n-butyl-tin)-oxide. The same yield was obtained. The melting regions was 75°-80° C. The elemental analysis was similar to the values given above.

EXAMPLE 4

30.38 g (0.1 mol) of di-i-butyl-tin dichloride are dissolved in about 100 ml of methanol and poured into a suspension of 15.4 g of sodium azide in methanol. After 4 hours' stirring, 4 g (0.1 mol) of NaOH are added; thereafter a little toluene (50 ml) is added and the methanol, which dissolves small amounts of sodium azide, is distilled off. The liquid is filtered off from the precipitated sodium salts and the toluene is removed in vacuum. A product like that in Example 2 precipitates in 97% yield (28 g).

EXAMPLE 5

27.6 g (0.10 mol) of di-propyl-tin-dichloride are dissolved in 100 ml of ether and let flow into a solution of 7.15 g (0.11 mol) of NaN$_3$ in 60 ml of water and 40 ml of acetone. After stirring for 4 hours at room temperature, 4 g of NaOH (0.1 mol) are added. The ether phase is separated in a separatory funnel and freed of ether after drying over Na$_2$SO$_4$. A solid white residue of bis-(azido-di-propyl-tin)-oxide remains in 24.2 g yield: that is 91.8 % of theory. IR spectrum clearly shows the azide bands at 2080-2095 cm$^{-1}$. The sample melts at 87° C but first clearly flows together only at 160° C. Analysis: C found = 28.53 (27.30%); H = 5.69 (5.69); N = 13.78 (15.93%); Sn = 45.65 (45.01%).

EXAMPLE 6

33.2 of di-pentyl-tin dichloride is treated as in Example 5. The residue of bis-(azido-di-pentyl-tin)-oxide weighs 30 g (93.8% of theory). It appears slightly yellowish and has a waxy consistency. Its flow point is between 59°-60°C. The IR-spectrum shows the azide bands at 2080-2095 cm$^{-1}$. Analysis: C found = 38.09 (37.53%); H = 7.43 (7.19%); N = 10.94 (13.14%); and Sn = 37.11 (37.13%).

What is claimed is:

1. A bis-(azido-di-alkyl-tin)-oxide of the formula

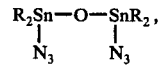

wherein R is alkyl having 3-5 carbon atoms.

2. A compound as in claim 1 which is bis-(azido-di-n-propyl-tin)-oxide.

3. A compound as in claim 1 which is bis-(azido-di-n-butyl-tin)-oxide.

4. A compound as in claim 1 which is bis-(azido-di-isobutyl-tin)-oxide.

5. A compound as in claim 1 which is bis-(azido-di-n-pentyl-tin)-oxide.

6. A bactericidal or fungicidal composition comprising a bactericidally- or fungicidally-effective amount of a compound as in claim 1 and a carrier therefor.

* * * * *